United States Patent
Gaserod et al.

(10) Patent No.: US 8,980,312 B2
(45) Date of Patent: Mar. 17, 2015

(54) SEAMLESS ALGINATE CAPSULES

(75) Inventors: Olav Gaserod, Steinberg (NO); Christian Klein Larsen, Lillestrom (NO); Peder Oscar Andersen, Oslo (NO)

(73) Assignee: FMC Corporation, Philadelphia, PA (US)

( * ) Notice: Subject to any disclaimer, the term of this patent is extended or adjusted under 35 U.S.C. 154(b) by 716 days.

(21) Appl. No.: 12/874,567

(22) Filed: Sep. 2, 2010

(65) Prior Publication Data

US 2011/0059165 A1    Mar. 10, 2011

Related U.S. Application Data

(60) Provisional application No. 61/241,263, filed on Sep. 10, 2009, provisional application No. 61/241,266, filed on Sep. 10, 2009.

(51) Int. Cl.
| | | |
|---|---|---|
| A61K 9/48 | (2006.01) | |
| A61K 35/60 | (2006.01) | |
| A61P 3/02 | (2006.01) | |
| B01J 13/20 | (2006.01) | |
| B01J 13/04 | (2006.01) | |
| A23L 1/00 | (2006.01) | |
| A61K 47/02 | (2006.01) | |
| A61K 47/36 | (2006.01) | |

(52) U.S. Cl.
CPC ............. *B01J 13/046* (2013.01); *A23L 1/0029* (2013.01); *A61K 9/4808* (2013.01); *A61K 9/4816* (2013.01); *A61K 9/4833* (2013.01); *A61K 47/02* (2013.01); *A61K 47/36* (2013.01); *B01J 13/206* (2013.01)
USPC .............................. 424/451; 424/523; 264/4.3

(58) Field of Classification Search
USPC .................................... 424/451, 523; 264/4.3
See application file for complete search history.

(56) References Cited

U.S. PATENT DOCUMENTS

| | | | |
|---|---|---|---|
| 3,376,199 A | | 4/1968 | Coles et al. |
| 4,520,142 A | * | 5/1985 | Leinen .......................... 523/205 |
| 4,702,921 A | | 10/1987 | Ueda |
| 5,139,783 A | | 8/1992 | Handjani et al. |
| 5,385,737 A | | 1/1995 | Shigeno et al. |
| 5,502,077 A | | 3/1996 | Breivik et al. |
| 5,942,266 A | | 8/1999 | Okamura et al. |
| 6,319,518 B1 | | 11/2001 | Lee et al. |
| 6,334,968 B1 | * | 1/2002 | Shapiro et al. ................... 264/28 |
| 6,458,818 B1 | | 10/2002 | Lipari et al. |
| 6,982,095 B2 | | 1/2006 | Asada et al. |
| 7,585,538 B2 | | 9/2009 | Mangos et al. |
| 2005/0019294 A1 | | 1/2005 | Modliszewski et al. |
| 2005/0106233 A1 | * | 5/2005 | Andersen et al. .............. 424/451 |

FOREIGN PATENT DOCUMENTS

| | | |
|---|---|---|
| EP | 0480729 | 4/1992 |
| JP | 11-076369 | 3/1999 |
| WO | WO 99/02252 | 1/1999 |
| WO | WO 03/084516 A1 | 10/2003 |

OTHER PUBLICATIONS

Oh et al. Journal of the American Board of Family Medicine, 2005, 18 (1), 28-36.*
The International Search Report and the Written Opinion of the International Searching Authority, or the Declaration Dated May 30, 2011, International Application No. PCT/US2010/047652.

* cited by examiner

*Primary Examiner* — Gina Justice
*Assistant Examiner* — Genevieve S Alley
(74) *Attorney, Agent, or Firm* — FMC Corporation

(57) ABSTRACT

The present invention is directed to a dried seamless capsule comprising an alginate shell membrane encapsulating fill material, wherein: (i) the alginate shell membrane comprises a polyvalent metal ion alginate having: (a) an average M content of from 50%-62% by weight based on the weight of the M and G content, and (b) a viscosity of 35 to 80 cps; (ii) the alginate shell membrane encapsulates an oil present in an amount of at least 50% by weight of the fill material; (iii) the dried seamless capsule has a disintegration time of less than 12 minutes in an intestinal buffer after pretreatment for 20 minutes; and (iv) the dried seamless capsule has a dry break force strength of at least 7 kg.

16 Claims, 4 Drawing Sheets

SEAMLESS ALGINATE CAPSULES

FIELD OF THE INVENTION

The present invention is directed to dried seamless capsules comprising an alginate shell membrane encapsulating a fill material and methods of manufacture and use thereof.

BACKGROUND OF THE INVENTION

Seamless alginate capsules having a variety of desirable characteristics are described in WO 03/084516. Seamless alginate capsules having an alginate in the shell membrane possessing a relatively high amount of G blocks provide strong capsules when compared to capsules having an alginate in the shell membrane possessing a relatively high amount of M blocks. However, seamless alginate capsules having a high G alginate content in the shell membrane have not been found to have fast disintegration in gastric environment, and, generally, gels made of high-M alginates generally have a poor mechanical strength compared to gels made of high-G alginates. Furthermore, increasing the concentration of an alginate having a high M content in the shell membrane would be expected to unacceptably increase process viscosity and create very difficult processing conditions, while decreasing the molecular weight of such an alginate would be expected to undesirably result in further weakening the (already very weak) capsules even at high concentrations.

It is desired, therefore, to develop a seamless alginate capsule that has the desired capsule strength and disintegration profile in gastric environment while solving the processing difficulties associated with capsule manufacture. The inventors tested numerous alginates varying M content, molecular weight and concentration, among other variables, and unexpectedly found a suitable process that provides capsules having unexpected strength and disintegration in the gastrointestinal environment.

SUMMARY OF THE INVENTION

The invention comprises a dried seamless capsule comprising an alginate shell membrane encapsulating a fill material, wherein: (i) said alginate shell membrane comprises a polyvalent metal ion alginate having: (a) an average M content of from 50%-62% by weight based on the weight of the M and G content, and (b) a viscosity of 35-80 cps when measured as a monovalent metal ion alginate in a 3.5% water solution at 20° C. using a Brookfield LV viscometer at 60 rpm and spindle #1; (ii) said alginate shell membrane encapsulates an oil present in an amount of at least 50% by weight of said fill material; (iii) said dried seamless capsule has a disintegration time of less than 12 minutes in an intestinal buffer after pretreatment for 20 minutes in a solution of 0.1 M NaCl and HCl, pH of 3, at 37° C.; and (iv) said dried seamless capsule has a dry break force strength of at least 7 kg. The present invention is also directed to methods of making and using such dried seamless capsules.

Applicants have surprisingly found that the capsules of the present invention (having both a quick disintegration time in intestinal buffer and a high break force strength) could be obtained by careful control of the process conditions (e.g., process viscosities in the gelling bath) and selection of the both the type of alginate and manipulation of its viscosity.

DETAILED DESCRIPTION OF THE INVENTION

Figure 1:
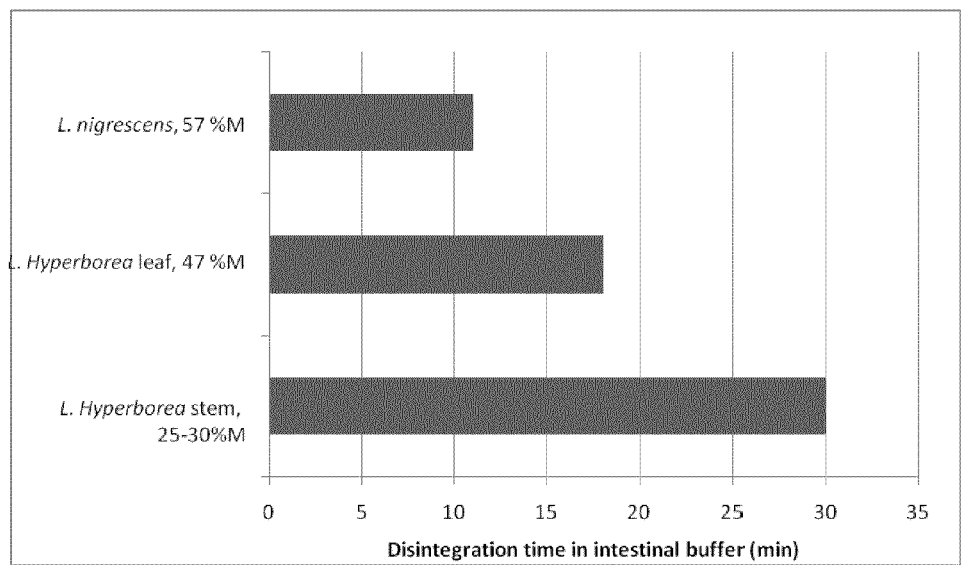
FIG. 1 illustrates disintegration time of capsules prepared without NaCl in the gelling bath.

Alginates, derived from, inter alia, brown seaweeds (Phaeophyceae sp.) are linear, unbranched chemical polymers containing (1-4)-linked β-D-mannuronic acid (M) and α-L-guluronic acid (G) residues. Alginates are not random copolymers, but consist of blocks of similar and alternating residues, for example, MMMM, GGGG, and GMGM, and are generally useful in the form of alginic acid or salts thereof.

The dried seamless capsule of the present invention has an alginate shell membrane comprising alginate. The alginate used to prepare the capsules has: (a) an average M content of from 50%-62% by weight of the M and G content, and (b) a viscosity of 35-80 cps when measured in a 3.5% water solution at 20° C. using a Brookfield LV viscometer at 60 rpm and spindle #1.

More particularly, the average M content of the alginate, by weight of the M and G content in the alginate, can be 51%, 52%, 53%, 54%, 55%, 56%, 57%, 58%, 59%, 60%, 61% or 62%. The M content may also be in the range of from 53% to 59% by weight of the M and G content in the alginate.

Alginate having an M content of the present invention is typically obtained from a variety of alginate producing seaweeds. The M content in seaweeds can vary depending on their life cycle at harvest, plant specificity, etc. Seaweeds generally considered to produce alginate having an M content of the present invention include Lessonia nigrescens (50-62% M), Laminaria digitata (about 59% M), Macrocystis pyrifera (about 60% M), Ecklonia maxima and Laminaria saccharina. It is also within the scope of the present invention to use a blend of alginates having various M contents provided the M content of all alginates in the blend have an average M content of from 50-62% M by weight of the M and G content in all of the alginate. The average M content in alginate is typically determined by $^1$H-NMR. The alginate can typically be extracted from the seaweed using, for example, standard commercial extraction processes such as an aqueous process including an acidic pretreatment followed by an alkaline extraction. Such conventional techniques are incorporated herein by reference.

Next, since the extracted alginates of the present invention having an average M content of 50-62% M typically have a high molecular weight and, thus, a high viscosity such as 200-1,000 cps in a 1% water solution, the alginate must then be degraded to obtain a viscosity of from 35 to 80 cps when measured in a 3.5% water solution at 20° C. using a Brookfield LV viscometer at 60 rpm and spindle #1. The degradation is typically done by conventional heat treatment processes of the alginic acid. These conventional processes are incorporated herein by reference. It is possible to use alginates having varying viscosities outside the scope of 35-80 cps as measured herein provided the resulting viscosity of all alginates used is within the range of from 35 to 80 cps.

The dried seamless capsules of the present invention desirably have a disintegration time of less than 12 minutes in an intestinal after pretreatment for 20 minutes in a solution of 0.1 M NaCl and HCl, pH of 3, at 37° C. and a dry break force strength of at least 7 kg. More particularly, the dried seamless capsule of the present invention may have a disintegration time of less than 10 minutes, less than 8 minutes, less than 6 minutes, in an intestinal buffer after pretreatment for 20 minutes in a solution of 0.1 M NaCl and HCl, pH of 3, at 37° C.

Furthermore, the dried seamless capsule of the present invention may have a dry break force strength of at least 10 kg, 12 kg, at least 15 kg, at least 16 kg, at least 17 kg, at least 18, kg, at least 19 kg, at least 20 kg, at least 21 kg, at least 22 kg, at least 23 kg, at least 24 kg, at least 25 kg, at least 26 kg, at least 27 kg, at least 28 kg, or at least 29 kg. The break force strength is measured using a SMS texture analyzer fitted with parallel plates with the capsules lying flat (not on their ends).

The intestinal buffer, as used herein, is a simulated intestinal buffer based on USP 28, chapter <2040>, page 2858, except pancreatin is not used. More specifically, the intestinal buffer is made by dissolving 136.0 g $KH_2PO_4$ (Merck, Lot A585477) in 5 L of deionized water, adding 61.6 ml 5N NaOH in 10 L deionized water, adjusting pH to 6.8 and diluting to a final volume of 20 L. The disintegration measurement is as described in the examples and in USP 28, chapter <2040>, including the chapter about 'Delayed-release (Enteric coated) tablets (incorporated herein by reference).

The presently claimed capsules having both the quick disintegration time in simulated intestinal buffer without pancreatin and a high break force strength was not expected because alginates having the claimed M content and viscosity would be expected to make very weak capsules that would not be suitable for many pharmaceutical, nutraceutical and veterinary applications.

The dried seamless capsules of the present invention encapsulate an oil in an amount of at least 50% by weight of the fill material. The oil itself can be an active ingredient such as a food or a pharmaceutical, nutraceutical, veterinary active ingredient or it can be a carrier for a food or an active ingredient such as a pharmaceutical, nutraceutical or veterinary active agent. When the oil is used as a carrier for a food or an active ingredient such as a pharmaceutical, nutraceutical or veterinary active agent, the food or an active ingredient such as a pharmaceutical, nutraceutical or veterinary active agent can be dissolved in the oil or dispersed in the oil. Examples of pharmaceutical active ingredients that may be dissolved or dispersed in the oil include all active ingredients useful to treat various cardiovascular and metabolic conditions such as statins. Other drugs that can be solubilised in the oil include amprenavir, agenerase, bexarotene, calcitrol, clofazimine, cyclosporine A, digoxin, drunabinol, dutasteride, etoposide, isotretanoin, lopinavir, itraconazole, loratidine, nifedipine, nimodipine, phenobarbitol, progesterone, risperidone, ritonavir, saquinavir, sirolimus, tretinoin and valproic acid.

The oil may be selected from any oil, or combination of oils, that find utility in an encapsulated form, for example, for use in the pharmaceutical, veterinary, nutraceutical, and food industries. Suitable oils include, without limitation, oils derived from marine and non-marine sources including fish, animals, plants, microorganisms, or extracts thereof oils that are chemical compounds derived by synthetic or other means, or formulations thereof or oils that are fatty acids, esters, salts or derivatives thereof. Such oils include triglyceride vegetable oils, commonly known as long chain triglycerides such as castor oil, corn oil, cottonseed oil, olive oil, peanut oil, safflower oil, sesame oil, soybean oil, hydrogenated soybean oil and hydrogenated vegetable oils; medium chain triglycerides such as those derived from coconut oil or palm seed oil, monoglycerides, diglycerides and triglycerides In addition to mixed glycerides there are other oils such as esters of propylene glycol such as mixed diesters of caprylic/capric acids of propylene glycol, esters of saturated coconut and palm kernel oil-derived caprylic, linoleic, succinic or capric fatty acids glycerin or propylene glycol and esters formed between fatty acids and fatty alcohols such as esters formed between capric or caprylic acid and glycerol. Garlic oil may also be used. Other oils within the scope of the present invention are those that include naturally occurring emulsifiers. One such oil is soy oil, which contains lecithin. Lecithin is useful in food manufacturing as an emulsifier in products high in fats and oils. Preferred oils within the scope of the present invention are those that are a liquid, or that can be made into a liquid at a temperature in the range of, for example, 20° C. to 95° C.

Oils that are fatty acids, salts, esters or derivatives thereof are useful in the present invention and are currently the subject of great commercial interest as a result of their beneficial health effects, for example, in reducing risk factors for cardiovascular disease and in the treatment of various metabolic disorders. Oils containing omega-3-fatty acids, salts, esters or derivatives thereof may be used in the present invention. Examples of oils containing such fatty acids, salts, esters or derivatives thereof include marine oils (e.g., fish oils) that are in the crude or concentrated form. Such marine oils contain important omega-3 polyunsaturated fatty acids such as (all-Z omega-3)-5,8,11,14,17-eicosapentaenoic acid (EPA) and (all-Z omega-3)-4,7,10,13,16,19-docosahexaenoic acid (DHA) that may be contained in varying ratios in the oil of the present invention. One example of such an oil that is useful in the present invention contains at least 80% by weight omega-3-fatty acids, salts or derivatives thereof, wherein the EPA and DHA is present in an amount of at least 75% by weight of the total fatty acid content. See, for example, U.S. Pat. No. 5,502,077. Any oil containing DHA and EPA from any source in any DHA/EPA ratio may be used in the present invention. Furthermore, any saturated, unsaturated, monounsaturated or polyunsaturated fat, oil, free fatty acid, esterified fatty acid from sources like vegetables, animals, fish, or microorganisms or synthetic may be used in the present invention.

The oil is present in the fill material of the capsules in an amount of at least 50% by weight of the fill material, more particularly, at least 60% by weight of the fill material, at least 70% by weight of the fill material, at least 80% by weight of the fill material, at least 90% by weight of the fill material, and at least 95% by weight of the fill material.

The oil in the fill material can also be in an emulsion such as a water in oil emulsion, oil in water emulsion or water in oil in water emulsion.

Drugs can be suspended in the oil, which drugs include those from the classes of gastro-intestinal drugs, anti-inflammatory drugs such as non steroidal anti inflammatory drugs, anti microbial drugs, drugs used in the treatment of pain, drugs used to treat metabolic disorders such as obesity, diabetes and rheumatoid arthritis.

The present invention is also directed to a method of making a seamless alginate capsule comprising an alginate shell membrane encapsulating a fill material, wherein the method comprises the steps of: (a) preparing an emulsion comprising oil, water, an emulsifier, and at least one of a water-soluble polyvalent metal salt or an acid, wherein the oil is present in an amount of at least 50% by weight of the oil, water, emulsifier, water-soluble polyvalent metal salt and acid; (b) adding portions of the emulsion to an aqueous gelling bath comprised of a monovalent metal ion alginate having (i) an average M content of from 50%-62% by weight of the M and G content, and (ii) a viscosity of 35-80 cps when measured in a 3.5% water solution at 20° C. using a Brookfield LV viscometer at 60 rpm and spindle #1; wherein said gelling bath comprises said alginate in an amount of 3-4% by weight of said gelling bath, thereby encapsulating said portions of said emulsion in said alginate shell membrane, and optionally (c) drying the resulting capsules by removing water.

The alginate of the invention that is present in the gelling bath is typically an alginate that is dissolved in the gelling bath such as sodium alginate. When the emulsion containing the polyvalent metal salt or acid is added to the gelling bath, the alginate shell membrane (e.g., calcium alginate) is formed.

The amount of the alginate in the gelling bath was determined to provide a key control of the process viscosities in the preparation of the capsules of the present invention. Applicants determined that in order to make the capsules of the present invention, the amount of the alginate used in the gelling bath is from 3-4% by weight of the gelling bath, more particularly, 3.25%-3.75% by weight of the gelling bath. More particularly, the alginate may be contained in the gelling bath in an amount of 3.5% by weight of the gelling bath. The process viscosities of the gelling bath are typically determined by a Brookfield LV viscometer with appropriate spindles and speeds for the target range.

Applicants have determined that the amount and type of the alginate in the gelling bath is a key control of the process viscosity and that process viscosity must be carefully controlled if capsules are to be successfully prepared. As set forth in the Examples, when using the alginate of the present invention, process viscosities are too low and too high when the alginate of the present invention is used in an amount outside the range of 3-4 wt % by weight in the gelling bath. Process viscosities that are too low and too high result in some cases in the inability to make capsules at all and, in other cases, in making capsules having numerous defects that are not suitable for pharmaceutical, veterinary and nutraceutical applications.

In addition, the agitation of the capsule fragments in the alginate bath and the viscosity of the alginate are connected in being able to successfully make capsules. Alginates having viscosities that require agitation that is too vigorous will deform or destroy the emulsion fragments, while alginates having viscosities that require very little agitation will result in capsule fragments staying attached to each other either temporarily or permanently. In the first instance, a hole in the shell is formed where the capsule fragments break apart, resulting in leaking capsules. In the second instance, double or twin capsules will be created, containing a double dose and therefore will need to be separated from the batch and discarded. End-to-end twin capsules may survive the gelling step and break apart later in the process, contaminating the other capsules with the emulsion. The viscosity of the alginate of the present invention enables appropriate agitations to be employed in the gelling bath that do not cause the problems described hereinabove. The inventors have observed that gelling bath viscosities below 30 cP and above 100 cP undesirably provide more of the problems described above when standard agitation techniques (such as stirring, vibration, or continuous flow over baffles) are employed.

The gelling bath may further contain at least one monovalent salt. The monovalent salt may be at least one of sodium chloride and potassium chloride. Particularly, the monovalent salt may be sodium chloride. The monovalent salt may be present in the gelling bath in an amount of from 0.1-0.5% by weight of the gelling bath, more particularly, in an amount of 0.3% by weight of the gelling bath.

In the process of the present invention, when a polyvalent salt such as calcium chloride reacts with the alginate (e.g., sodium alginate) in the gelling bath, sodium chloride is generated. Generally, the presence of monovalent salts normally interferes with the reaction between the gelling polyvalent salt and the alginate and this can have a negative impact on the resulting gel properties. If the monovalent salt is not added to the alginate solution initially, the concentration of monovalent salts will be practically zero at the start and increase significantly during the process, in particular, if a continuous production mode is chosen. This will result in different capsule quality of the capsules made first as compared with the capsules made later in the batch. The addition of a monovalent salt in the gelling bath has been surprisingly found to provide a preferred means of providing a stable level of monovalent salts during continuous capsule production, ensuring consistent quality of the capsules both in the wet and dry state.

The gelling bath or a separate bath may also contain additional components including, without limitation, dyes, colorants, plasticizers, emulsion destabilizers, density adjusters, preservatives, antioxidants, solids, disintegrants, antifoaming agents and other components. Examples of the plasticizer that can be used include glycerol, noncrystallizing sorbitol such as Polysorb 85/70/00 (Roquette), sorbitol special, maltitol and polyethylene glycols, propylene glycol, or combinations of plasticizers.

In one embodiment, the shell membrane of the seamless alginate capsule comprises glycerol and a noncrystallizing plasticizer, wherein a weight ratio of the noncrystallizing plasticizer to glycerol is between about 1:1 and about 8:1. In another embodiment, the ratio is between about 2:1 and about 6:1. In yet another embodiment, the ratio is between about 2:1 and 4:1. More specifically, the ratio can be about 1:1, about 2:1, about 3:1, about 4:1, about 5:1, about 6:1, about 7:1, or about 8:1. The glycerol can comprise between about 6% (wt/wt) and about 22% (wt/wt) of the shell membrane and the noncrystallizing plasticizer can comprise between about 6% (wt/wt) and about 54% (wt/wt) of the shell membrane. More particularly, the glycerol in the shell membrane can be about 14% and the noncrystallizing plasticizer can be about 36% by weight.

By the term "noncrystallizing plasticizer" is meant a compound or composition that decreases blooming or recrystallization of the plasticizer substance in or on the capsule shell membrane. Glycerol is excluded from the definition of noncrystallizing plasticizer. The noncrystallizing plasticizer can comprise or consist essentially of a mixture of sugar alcohol (s) and dehydro sugar alcohols. The noncrystallizing plasticizer can be "noncrystallizing sorbitol," which is a mixture of sorbitol and anhydrized sorbitol. POLYSORB® 85/70/00 (Roquette, Lestrem, France) is a suitable noncrystallizing sorbitol. POLYSORB® 85/70/00 is an aqueous solution of 35-45% (wt/wt) sorbitol and 24-28% 1,4-sorbitans (wt/wt) obtained through a partial internal dehydration of sorbitol. POLYSORB® 85/70/00 has about 83% solids content. Sorbitol Special Polyol Solution® (SPI Pharma, Wilmington, Del., USA) is also a suitable noncrystallizing sorbitol. In one embodiment, the noncrystallizing plasticizer can include maltitol, fructose, or polyoxyethylene glycols.

WO 03/084516 discloses typical process conditions and examples of the other components that may be used in the present invention and such disclosure is incorporated herein by reference in its entirety.

Emulsifiers suitable in the context of the present invention are chemical compounds having both a hydrophilic group and lipophilic group wherein the HLB value is in the range of 1 to 19. Examples of such emulsifiers having HLB values in the range of 1 to 19 include, without limitation, glycerin fatty acid esters, lactic acid esters of monoglycerides, lecithins, polyglycerol polyricinoleate, sorbitan esters of fatty acids acids such as polyoxyethylene(20) sorbitan monooleate, sorbitan monooleate and polyoxyethylene(25) glycerol trioleate, polyoxyethylene(20) sorbitan, succinic acid esters of monoglycerides, calcium stearoyl dilactate, citric acid esters of monoglycerides, diacetyl tartaric acid esters of monoglycerides, polyoxyethylene sorbitan esters of fatty acids, sucrose esters of fatty acids, and other emulsifiers. Emulsifying agents may also include some particulate materials, such as, for example, soot (water-in-oil emulsion stabilizer) or silica powder (oil-in-water emulsion stabilizer) as generally known. Preferred emulsifiers of the present invention are selected from the group of polyoxyethylene(20) sorbitan monopalmitate (sold under the name TWEEN 40) polyglycerol polyricinoleate (sold under the name and trademark of PGPR 90, by Danisco, Copenhagen, Denmark), calcium stearoyl-2-lactylate (sold under the name and trademark of VERV K, by American Ingredients Company, Kansas City, Mo., USA), sorbitan monooleate (sold under the name and trademark of SPAN 80, by Aldrich Chemical, Milwaukee, Wis., USA), and mixtures thereof. More preferred emulsifiers are polyoxyethylene(20) sorbitan monopalmitate, polyglycerol polyricinoleate, or mixtures thereof.

The emulsions of oil, emulsifier and water of the present invention contain at least one of a water-soluble polyvalent metal salt or an acid. A water-soluble polyvalent metal salt or acid suitable for use in the present invention includes any inorganic or organic salt or acid that is capable of disassociating into a free ionic state in water, where the ions are capable of forming a gel with the alginate. Suitable salts include, without limitation, the salts of calcium, strontium, barium, aluminum, magnesium, zinc, other salts, and mixtures thereof. A preferred salt is calcium chloride, in either hydrated or anhydrous form. Increasing the salt content in the oil and water emulsion, inter alia, increases the thickness of the polysaccharide gel membrane when the capsules are formed. The salt in the oil and water emulsion is present in at least a gel-forming amount sufficient to adequately form alginate shell membranes surrounding portions of the oil and water emulsion. Preferably, within the scope of the present invention, the salt is present in the oil and water emulsion in an amount of up to 25% by weight of the emulsion, more preferably, from 2% by weight to 15% by weight of the emulsion.

In a first embodiment of the present invention, the emulsion is an oil-in-water emulsion. The emulsion can be prepared by dissolving a polyvalent metal salt (as discussed above), for example, calcium chloride dihydrate and at least one emulsifier (as discussed above) for example, polyoxyethylene(20) sorbitan monopalmitate, in water. The resultant solution may then be homogenized during which time the oil can be slowly added to form a highly viscous oil-in-water emulsion. A preferable amount of oil present in the oil-in-water emulsion is in an amount of 70% by weight to 98% by weight of the oil, water, emulsifier and water-soluble polyvalent metal salt and acid, more preferably, in an amount of 85% by weight to 95% by weight of the oil, water, emulsifier and water-soluble polyvalent metal salt and acid.

In a second embodiment of the present invention, the emulsion is a water-in-oil emulsion. The emulsion can be prepared by adding a water solution of a polyvalent metal salt (as discussed above) and at least one emulsifier (as discussed above), for example, polyglycerol polyricinoleate, to an oil (as discussed above) during which time the mixture can be homogenized to provide the water-in-oil emulsion. A preferable amount of oil present in the water-in-oil emulsion is in an amount of 65% by weight to 85% by weight of the oil, water, emulsifier and water-soluble polyvalent metal salt and acid, more preferably, in an amount of 70% by weight to 80% by weight of the oil, water, emulsifier and water-soluble polyvalent metal salt and acid. As set forth above, soy oil contains the naturally occurring emulsifier lecithin. Water-in-oil emulsions of soy oil may be stable for a period of time long enough so that the emulsion can be encapsulated without inclusion of additional emulsifier.

In a third embodiment of the present invention, the emulsion is a water-in-oil-in-water emulsion. A water-in-oil-in-water emulsion provides a means for encapsulating not only an oil, or an oil-soluble substance, but also, a water-soluble substance, or a water-soluble active ingredient. Accordingly, an inner phase comprised of a solution of a water-soluble substance in water can be added to a middle phase comprised of an oil (as discussed above) and an emulsifier (as discussed above), for example, polyglycerol polyricinoleate, during which time the mixture can be homogenized to form a water-in-oil emulsion. The so-formed water-in-oil emulsion may then be added to an outer phase comprised of a water solution of a polyvalent metal salt (as discussed above) and an emulsifier (as discussed above), for example, polyoxyethylene(20) sorbitan monopalmitate, during which time the mixture can be homogenized to form a highly viscous water-in-oil-in-water emulsion. A preferable amount of oil present in the water-in-oil-in-water emulsion is in an amount of 60% by weight to 90% by weight of the oil, water, emulsifier and water-soluble polyvalent metal salt and acid, more preferably, in an amount of 70% by weight to 80% by weight of the oil, water, emulsifier and water-soluble polyvalent metal salt and acid.

A preferred emulsion in the context of the present invention is an oil-in-water emulsion as discussed above in the first embodiment. A drying process at an elevated temperature and high air flow, for example, at about 30° C. and 0.5-5 m/s, to remove water from the oil-in-water emulsion prior to its encapsulation can eliminate a large portion of water from the encapsulation step, thereby providing a capsule in a relatively dry form, if a capsule in dry form is desired. The length of a separate capsule-drying step can therefore be shortened. Additionally, as an aid to shortening the length of a capsule-drying step if one is desired, some of the water in the emulsion can be replaced with a water-miscible solvent, for example an alcohol of $C_1$-$C_4$ straight or branched carbon length, for example, ethanol.

The seamless capsules of the present invention may also contain encapsulated materials other than the oil. These additional encapsulated materials may be any oil or water soluble pharmaceutical, nutraceutical and veterinary active ingredients. Thus, such additional encapsulated materials may be dissolved in the oil or dispersed therein.

The capsules of the present invention may take any shape such as spherical, oval, cylindrical or oblong. They may be in dry form may have varying capsule diameters depending on the intended use; e.g., the capsule diameter can be relatively small or somewhat larger, and be in the range of 0.5 millimeter to 35 millimeters, where the alginate shell membrane generally has a thickness in the range of 40 μm to 500 μm. Gel membrane thickness of the capsules of the invention may be in the range of 0.3 millimeter to 4 millimeters.

Once dried, the capsules may contain water in the fill material in an amount of less than 5%, less than 3%, or between 0%-0.5%. Typically, once dried, the emulsion is no longer present in the fill material or it may be found in the form of a dehydrated emulsion maintaining its structure.

After capsule formation but before drying, the capsules may further be processed with a plasticizer solution such as glycerol, non-crystallizing sorbitol such as Polysorb 85/70/00 (Roquette), sorbitol special, maltitol and polyethylene glycols, propylene glycol, propylene glycol, alone or in combination.

All embodiments of the present invention include those where the fill material in the dried seamless capsule, as well as the emulsion used in the process of making the seamless alginate capsules, do not contain marmelo mucilage.

The present invention includes those seamless capsules wherein the alginate of the present invention is the only gel forming component in the shell membrane.

The present invention is now described in more detail by reference to the following examples, but it should be understood that the invention is not construed as being limited thereto. Unless otherwise indicated herein, all parts, percents, ratios and the like are by weight.

EXAMPLES

Example 1

Capsules Made from Alginate with Different M-Content—Influence on Disintegration Times The alginates used in this example were isolated from *Laminaria hyperborean* stems ($F_M$=not analyzed, but typically 0.25-0.35), *Laminaria hyperborean* leaves ($F_M$=0.47), and *Lessonia nigrescens* ($F_M$=0.57). The alginate solutions were made by simply dissolving the alginate to a 5% concentration, except for the Lessonia alginate sample that required degradation in molecular weight to lower the process viscosity. The alginate was dissolved to prepare an 8.3% solution, and kept at 85-90° C. for 3 hours. After a dilution to a 5% concentration the viscosity measured 106 cP at 22° C. measured with RV spindle 2 at 20 rpm on a Brookfield viscometer (this is approximately 38-40 cps when measured using a Brookfield LV viscometer, spindle #1 at 60 rpm). The dry matter content was measured using an infrared drier (Mettler Toledo HR73) to 4.05%. A set of gel baths was prepared for the different alginates containing 0.15% NaCl (see FIG. 2). The alginate solutions were kept in a slowly stirred tank, and a continuous flow of about 10 l/min was recirculated in a loop up from the tank and down steep, open flow (waterfall) down back into the tank. The temperature ranged from 22-26° C. A pre-emulsion was prepared by dissolving 210 g of calcium chloride dihydrate in 300 g water before further dissolving 60 g Polysorbate 40. While stirring, 3,900 g of fish oil was added slowly.

The following equipment was used in capsule production:

| Type | Model | Manufacturer |
|---|---|---|
| Homogeniser | Inline mixer, Lab unit LR4 | Silverson |
| Nozzle and holder | Custom made | Nisco/FMC |
| Emulsion pump | Moyno pump, Nemo NM011 | Netzsch |
| Frequency inverter for pump | DFE23-02 | Emotron |
| Emulsion tank | 5 L | — |
| Overhead stirrer | IKA RW16 basic | IKA |
| Anchor stirrer | R1333 | IKA |
| Gelling bucket | 40 L | |
| Cutting wire with weight | 0.102 mm line, 0.9 g weight. 10 cm cutting arm length. | |
| Cutter motor | Eurostar, Euro-ST P CV | IKA |
| Gelling bath pump | Lobe pump, OL range 1/0004 | Johnson |
| Frequency inverter for gelling bath pump | DFE23-04 | Emotron |

Capsules were made by pumping the pre-emulsion through the inline mixer, achieving a viscosity of about 60,000 to 90,000 cps, measured with a RVT-DV-III Viscometer, with a Helipath spindle T-E-spindle no. 95 at 10 rpm and 25° C. From there the emulsion was extruded through an 8.5 mm wide nozzle and cut into fragments using a rotating disk with two 0.102 mm nylon lines having alginate solution in the waterfall and they were fed into the alginate tank. The target fill weight of these capsules was 1000 mg. After a residence time of about 20 min, the capsules were retrieved and given a quick water rinse. The capsules were then kept in water for 3 hours at a capsule to water weight ratio of about 1:4, followed by a 30 min residence time in a plasticizer solution containing 15% of Sorbitol sorbitan solution (Sorbitol Special, SPI) at a capsule to plasticizer weight ratio of about 1:4. After this, the capsules were air dried at ambient conditions on a bench.

| | *L. hyperborea* stem | *L. hyperborea* leaf, $F_M$ = 0.47 | *L. nigrescens*, $F_M$ = 0.57 |
|---|---|---|---|
| Break strength, wet | 5.4 | 3.3 | 3.0 |
| Break strength, dry | 26.9 | 27.8 | 26.1 |

The break strength of the capsules was measured on a texture analyzer from Stable Microsystems using a flat probe. It would be expected that the break strength would decrease considerably as the M-content of the alginate increases. However, as set forth in the immediately preceding table, the break strength of the dry capsules having the claimed M content was unexpectedly very high and comparable to the dry capsules having less M content outside the scope of the present invention.

The capsules were tested for disintegration times using a basket disintegration apparatus B, each basket containing 3 compartments and disks. The capsules were placed there after a pretreatment of 9 capsules in 770 ml of a model gastric solution containing HCl to pH 3 and NaCl to 0.1 M at 37° C. The simulated intestinal fluid was made according to USP Simulated Intestinal Fluid, but without pancreatin. In detail, the solution was made by dissolving 136.0 g $KH_2PO_4$ (Merck, Lot A585477) in 5 L of deionized water, adding 61.6 ml 5N NaOH in 10 L deionized water, adjusting pH to 6.8 and dilute to a final volume of 20 L. The disintegration times was noted from the time the capsules were added to the simulated intestinal fluid. Specifically, the disintegration time in USP simulated Intestinal Fluid was measured after a 20 min pretreatment in a simulated gastric fluid composed of HCl to pH 3 and NaCl to a total ionic strength of 0.1 M.

Figure 2:
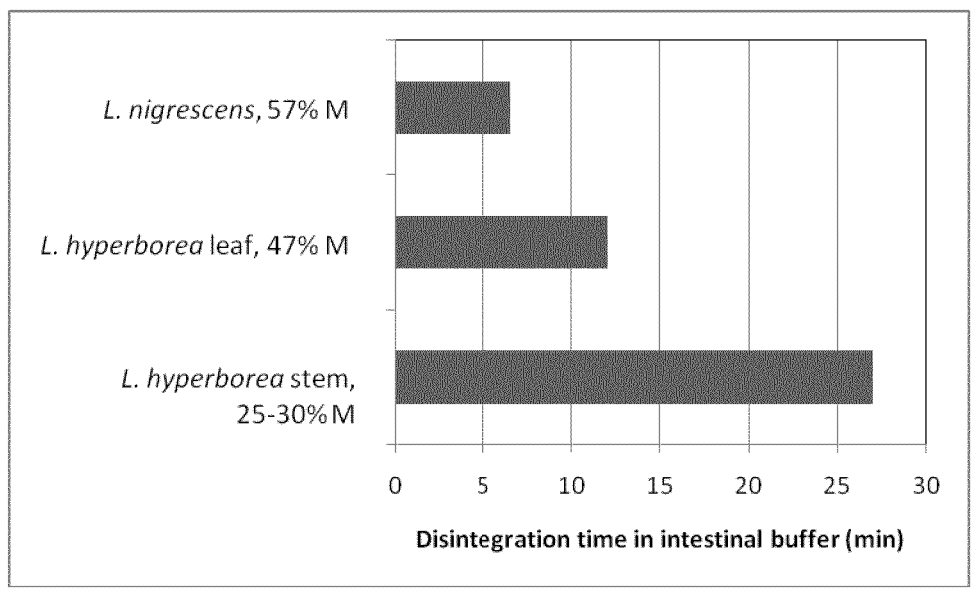
FIG. 2 illustrates disintegration time of capsules prepared with the gelling bath having 0.1 M NaCl.

FIG. 1 shows the disintegration times of capsules made from the alginates of different M-contents. Clearly, there is a distinct difference between the different alginate types showing that capsules made of high M/G ratio alginate disintegrate faster than capsules made from alginate with lower M/G ratio. The differences have also been observed after pre-treatment in weaker acidic solutions and salt solution, but also from shorter pre-treatment times, indicating that high M/G ratio alginate capsules are transformed into a weaker capsule faster than the high-G alginates. When adding NaCl to the gelling bath, disintegration times overall are further reduced which is seen in FIG. 2. Specifically, in FIG. 2, disintegration time in USP simulated Intestinal Fluid was measured after a 20 min pretreatment in a simulated gastric fluid composed of HCl to pH 3 and NaCl to a total ionic strength of 0.1 M. The viscosity of the gelling solution (106 mPas) is too high for larger scale processes, so modification to the composition of the alginate bath was needed.

Example 2

Comparative Example—Alginate Capsules Made with Alginate Having Viscosity Lower than the Invention Gave Capsules with Unacceptably Low Wet Break Strength and High Occurrence of Breakage During Drying The capsules in this example were made as in Example 1 with the following variations: the pre-emulsion was made using 3250 g Cod liver oil, added into an aqueous phase with a composition of 250 g deionized water, 175 g $CaCl_2*2H_2O$, and 25 g Polysorbate 40. The alginate bath was made using a combination of two alginate samples. 525 g of RENO 7029 (54% M content) and 225 g of RENO 7030 (53% M content), and 45 g NaCl was dissolved in deionized water to a total weight of 15,000 g. The pH of the solution was adjusted to 7 using a 2 M NaOH solution. The resulting solution had a total alginate concentration of 5% and a viscosity of 61.6 cP. The two alginate products are characterized by both being extracted from L. nigrescens seaweed, RENO 7029 (54% M content) had a viscosity of 2.5 cP in a 1% solution, and RENO 7030 (53% M content) had a viscosity 14.6 cP in a 1% solution. The viscosity of the two alginates in a 3.5% water solution would be estimated at 33 cps at 60 rpm and spindle #1. The capsules were washed in water overnight and plasticized for 25 min in a 15% glycerin solution. The capsules were placed on a bench for air drying at ambient conditions. During the drying process, about 42% of the capsules ruptured, indicating that the average molecular weight is so low that the integrity of the capsule shell is unacceptably low. The average break strength (n=3) of wet capsules after gelling was measured to 406 g, which is very low. Therefore, this example demonstrates what happens when capsules are made from the tested alginates having M content of 54% and 53%, respectively, and a viscosity at 33 cps.

Example 3

A Formulation of the Present Invention that Gives High Mechanical Strength Capsules and Acceptably Low Process Viscosity The capsules in this example were made as in Example 2 with the following variations. The alginate bath was made using a combination of two alginate samples. 225 g of RENO 7035 (50% M) and 300 g of RENO 7036 (53% M), and 45 g NaCl was dissolved in deionized water to a total weight of 15,000 g. The resulting solution had a total alginate concentration of 3.5% and a viscosity of 69 cP when measured at 60 rpm using spindle #1 (approximately 76 cP when measured in a 3.5% water solution using spindle #1 at 60 rpm). The two alginate products are characterized by both being extracted from L. nigrescens seaweed, RENO 7035 had a viscosity of 4.6 cP in a 1% solution, and RENO 7036 had a viscosity of 9.7 cP in a 1% solution. During washing the capsule to water weight ratio was about 1:3. The plasticizer solution contained 10% glycerin. No capsule rupture was seen during drying, and the average wet break strength (n=4) was measured to 1914 g, and the average dry break strength (n=4) was measured to 32,034 g.

Example 4

Effect of Alginate Concentration in the Gelling Bath

The capsules in this example were made with a blend of alginates isolated from L. nigrescens (e.g., having an average M content of from 50-62% by weight of the M and G content), having a final viscosity of approximately 57 cP when measured in a 3.5% water solution using spindle #1 at 60 rpm. The emulsion was prepared by dissolving 7 g of calcium chloride dihydrate in 10 g water before further dissolving 2 g Polysorbate 40. 130 g of fish oil was added in portions while use with the Ultra Turrax until the emulsion was formed. The viscosity of the emulsion was measured to 95,000 cP.

The emulsion was filled in a plastic bag attached to a nozzle. Fragments were made by squeezing the bag and manually cutting off about 1 g fragments using a scalpel. The fragments were let down in gelling baths of different alginate concentrations ranging from 2% to 5%. All baths contained 0.3% NaCl. The gelling time was about 20 minutes. After this the capsules were washed in water for 3 hours.

The shell thickness increased with increasing alginate concentration in the bath. Previous experience has shown the total amount of alginate in the shells depends on the calcium release, which would be equal for capsules coming from all the baths. Assuming constant alginate amount in all capsules and different shell thickness and thus shell volume, the concentrations of the plasticizer solutions were adjusted to target same alginate to plasticizer ratio in the final capsules.

| Film thickness (mm) | 1.35 | 1.2 | 1.1 | 1 | 0.9 |
|---|---|---|---|---|---|
| Glycerol concentration in plasticizing solution (%) | 8.1 | 9.2 | 10 | 11 | 12.2 |

The capsules were treated in the plasticizer solution for 25 min, before drying on a steel mesh surface for about 24 hrs. Within the first hour of drying the capsules were turned.

The break strength of the wet and dry capsules was measured on a SMS texture analyzer fitted with parallel plates. Capsule break strength was evaluated with capsules lying flat, not standing on end. The overall break strength were lower since the capsules here were made with manual cutting, leading to imperfections in the cut surface leading and thus weak points in the capsule shell. However, the trends were still significant important.

Figure 3:
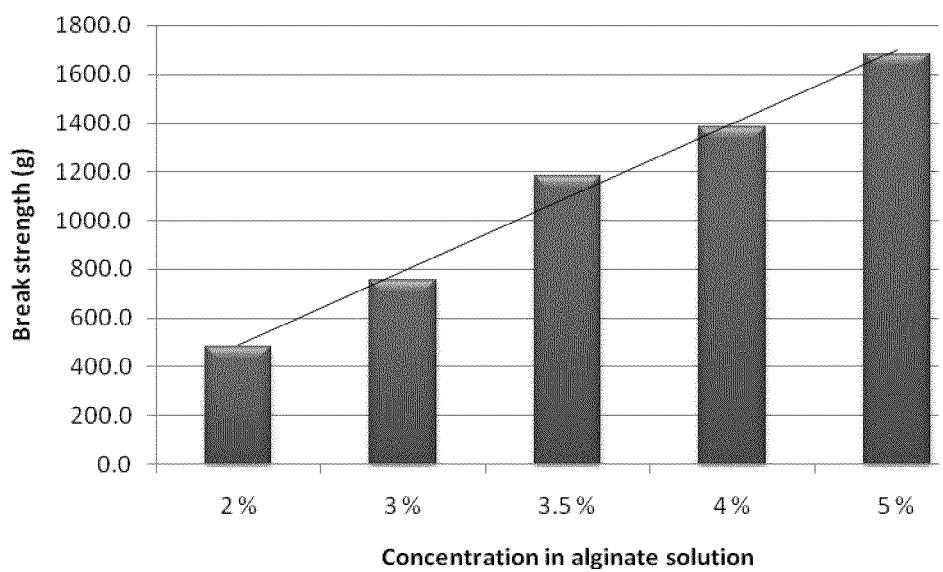
FIG. 3 illustrates the break strength of wet capsules.

For the wet capsules there was a clear trend whereby the break strength increased proportional with the concentration in the alginate bath. See FIG. 3. A high break strength here is desirable due to lower risk of broken capsules during processing. On the other hand, there was a limit as to how much alginate could be added to the bath to maintain an acceptably low process viscosity.

Figure 4:
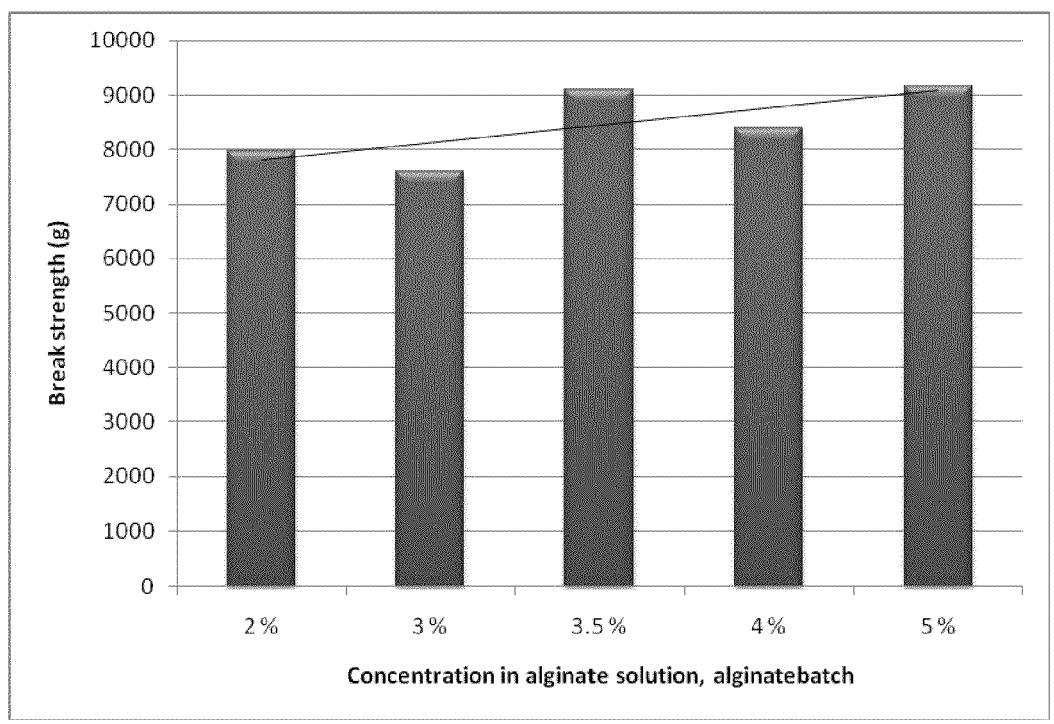
FIG. 4 illustrates the break strength of dry capsules.

For the dry capsules the break strength was less dependent on the alginate concentration in the bath (likely due to the final shell in all cases containing about the same amount of alginate and glycerin), but still there exists evidence that the break strength increased somewhat with increasing alginate concentration in the bath. See FIG. 4.

TABLE 4

| Viscosity of the gelling bath before capsule preparation. | | | | | |
|---|---|---|---|---|---|
| Alginate Amount | 2% | 3% | 3.5% | 4% | 5% |
| mPa · s | 20 | 37.5 | 52.5 | 75 | 145 |

Measured by Brookfield LV Viscometer, spindle 2 and 60 rpm.

Applicants have determined that process viscosities for the alginate of the invention below 30 cP and above 100 cP undesirably result in significant manufacturing problems such as mentioned hereinabove and, as the table immediately above demonstrates, that the amount of the alginate of the invention in the gelling bath should be between 3% and 4% by weight of the gelling bath in order to overcome these processing problems.

This Example demonstrates that the dried alginate seamless capsule of the present invention exhibits both acceptable strength and process viscosity during manufacture.

While the invention has been described in detail and with reference to specific embodiments thereof, it will be apparent to one skilled in the art that various changes and modifications can be made therein without departing from the spirit and scope thereof.

What is claimed is:

1. A dried seamless capsule comprising an alginate shell membrane encapsulating a fill material, wherein:
   (i) said alginate shell membrane comprises a polyvalent metal ion alginate wherein said alginate is the sole gel-forming component in the shell membrane and said alginate has: (a) an average M content of from 50%-62% by weight based on the weight of the M and G content, and (b) a viscosity of 35-80 cps when measured as a monovalent metal ion alginate in a 3.5% water solution at 20° C. using a Brookfield LV viscometer at 60 rpm and spindle #1;
   (ii) said alginate shell membrane encapsulates an oil present in an amount of at least 50% by weight of said fill material;
   (iii) said dried seamless capsule has a disintegration time of less than 12 minutes in an intestinal buffer after pretreatment for 20 minutes in a solution of 0.1 M NaCl and HCl, pH of 3, at 37° C.; and
   (iv) said dried seamless capsule has a dry break force strength of at least 7 kg.

2. The dried seamless capsule of claim 1, having a dry break force strength of at least 20 kg.

3. The dried seamless capsule of claim 1, wherein said dried seamless capsule has a disintegration time of less than 10 minutes in an intestinal buffer after pretreatment for 20 minutes in a solution of 0.1 M NaCl and HCl, pH of 3, at 37° C.

4. The dried seamless capsule of claim 1, wherein said alginate has an M content of from 53% to 59% by weight based on the weight of the M and G content.

5. The dried seamless capsule of claim 1, wherein said fill material comprises an oil that is a pharmaceutical, nutraceutical or veterinary active agent or a carrier for a pharmaceutical, nutraceutical or veterinary active agent.

6. The dried seamless capsule of claim 5, wherein said oil is a pharmaceutical, nutraceutical or veterinary active ingredient.

7. The dried seamless capsule of claim 6, wherein said oil comprises omega-3-fatty acids, salts, esters or derivatives thereof.

8. The dried seamless capsule of claim 1, wherein said capsule is made by a process comprising:
   (a) preparing an emulsion comprising oil, water, an emulsifier, and at least one of a water-soluble polyvalent metal salt or an acid, wherein said oil is present in an amount of at least 50% by weight of said oil, water, emulsifier, water-soluble polyvalent metal salt and acid;
   (b) adding portions of said emulsion to an aqueous gelling bath comprised of a monovalent metal ion alginate having (i) an average M content of from 50%-62% and (ii) a viscosity of 35-80 cps when measured in a 3.5% water solution at 20° C. using a Brookfield LV viscometer at 60 rpm and spindle #1; wherein said gelling bath comprises said alginate in an amount of 3-4% by weight of said gelling bath, thereby encapsulating said portions of said emulsion in said alginate shell membrane; and
   (c) drying the resulting capsules.

9. A method of preparing the dried seamless capsule of claim 1 comprising the alginate shell membrane encapsulating the fill material, comprising the steps of:
   (a) preparing an emulsion comprising oil, water, an emulsifier, and at least one of a water-soluble polyvalent metal salt or an acid, wherein said oil is present in an amount of at least 50% by weight of said oil, water, emulsifier, water-soluble polyvalent metal salt and acid;
   (b) adding portions of said emulsion to an aqueous gelling bath comprised of a monovalent metal ion alginate having (i) an average M content of from 50%-62% and (ii) a viscosity of from 35-80 cps when measured in a 3.5% water solution at 20° C. using a Brookfield LV viscometer at 60 rpm and spindle #1; wherein said gelling bath comprises said alginate in an amount of 3-4% by weight of the gelling bath, thereby encapsulating said portions of said emulsion in said alginate shell membrane, and optionally
   (c) drying the resulting capsules by removing water.

10. The method of claim 9, wherein the alginate is present in said gelling bath in an amount of from 3.25% to 3.75% by weight of the gelling bath.

11. The method of claim 10, wherein the alginate is present in said gelling bath in an amount of 3.5% by weight of the gelling bath.

12. The method of claim 9, wherein said gelling bath further comprises a monovalent salt.

13. The method of claim 12, wherein said monovalent salt comprises sodium chloride or potassium chloride.

14. The method of claim 13, wherein said monovalent salt is sodium chloride.

15. The method of claim 12, wherein said monovalent salt is present in said gelling bath in an amount of from 0.1-0.5% by weight of the gelling bath.

16. The method of claim 15, wherein said monovalent salt is present in said gelling bath in an amount of 0.3% by weight of the gelling bath.

* * * * *